(12) United States Patent
Kansy et al.

(10) Patent No.: US 6,887,432 B2
(45) Date of Patent: May 3, 2005

(54) CUVETTE ARRAYS

(75) Inventors: Manfred Kansy, Freiburg (DE);
Hansjörg Tschirky, Ettingen (CH);
Werner Schneider, Pfeffingen (CH);
Heinrich Büttgen, Rapperswil (CH);
Tilo Callenbach, Jona (CH); Karl Mazenauer, Jona (CH)

(73) Assignees: Hoffmann-La Roche Inc., Nutley, NJ (US); Weidmann Plastics Technology AG, Rapperswil (CH)

( * ) Notice: Subject to any disclaimer, the term of this patent is extended or adjusted under 35 U.S.C. 154(b) by 631 days.

(21) Appl. No.: 10/077,363

(22) Filed: Feb. 15, 2002

(65) Prior Publication Data
US 2002/0155035 A1 Oct. 24, 2002

(30) Foreign Application Priority Data

Feb. 20, 2001 (EP) .............................................. 01810178

(51) Int. Cl.$^7$ ................................................. B01L 3/00
(52) U.S. Cl. ........................ 422/102; 422/103; 422/104
(58) Field of Search ............................ 422/61, 99, 102, 422/103, 104; 220/23.2, 23.4, 23.6, 23.8

(56) References Cited

U.S. PATENT DOCUMENTS

| 3,785,773 A | | 1/1974 | Rohrbaugh |
| 4,263,256 A | * | 4/1981 | Morle .......................... 422/66 |
| 4,472,357 A | * | 9/1984 | Levy et al. .................. 422/102 |

(Continued)

FOREIGN PATENT DOCUMENTS

| DE | 197 30 445 | 1/1999 |
| EP | 0 339 769 | 11/1989 |
| EP | 0 415 307 | 3/1991 |
| EP | 0 688 602 | 12/1995 |

OTHER PUBLICATIONS

Manfred Kansy, et al., *Journal of Medicinal Chemistry*, vol. 7, pp. 1007–1010 (1998), no month.

*Primary Examiner*—Jeffrey R. Snay
(74) *Attorney, Agent, or Firm*—George W. Johnston; John P. Parise

(57) ABSTRACT

An integrally built, linear array of cuvettes is made of a plastic material. Every cuvette of the array has the same shape and dimensions. Neighboring cuvettes are connected to each other by a single web. Each of the single webs has a curved shape and each cuvette has means forming integral part thereof and serving for accurately positioning the cuvette into an opening of a cuvette holder and means for removably connecting the cuvette to the cuvette holder. Each cuvette has an upper chamber and a lower chamber having a common symmetry axis passing through the centers of both chambers. Each of the upper and lower chambers has a substantially cylindrical shape. The cross-section of the upper chamber at the central part thereof is larger than the cross-section of the lower chamber. The lower chamber has an open lower end. The upper chamber has an open top end and an annular bottom wall having a central circular opening which connects the upper chamber with the lower chamber. The inner surface of the bottom wall of the upper chamber (17) is part of a conical surface the cross-section of which forms an angle of about 80 degrees with the symmetry axis, so that there is an abrupt change of cross-section between the upper chamber and the lower chamber. A two-dimensional array of cuvettes comprises a plurality of linear cuvette arrays inserted into a cuvette holder having a matrix array of cuvette receiving openings. A system of two-dimensional cuvette arrays is built by stacking two or more of such two-dimensional arrays of cuvettes. Foil shaped layers serving, e.g. as a filter, are adapted to be attached to each cuvette to cover at least one opening thereof.

10 Claims, 6 Drawing Sheets

U.S. PATENT DOCUMENTS

| | | | | |
|---|---|---|---|---|
| 4,566,790 A | * | 1/1986 | Mandle | 356/246 |
| 4,799,599 A | | 1/1989 | Herrmann | |
| 4,902,479 A | * | 2/1990 | Brickus | 422/72 |
| 5,084,246 A | * | 1/1992 | Lyman et al. | 422/101 |
| 5,098,661 A | * | 3/1992 | Froehlich et al. | 422/102 |
| 5,470,536 A | * | 11/1995 | Jarvimaki | 422/102 |
| 5,571,479 A | | 11/1996 | Koch | |
| 5,720,406 A | | 2/1998 | Fassbind et al. | |

* cited by examiner

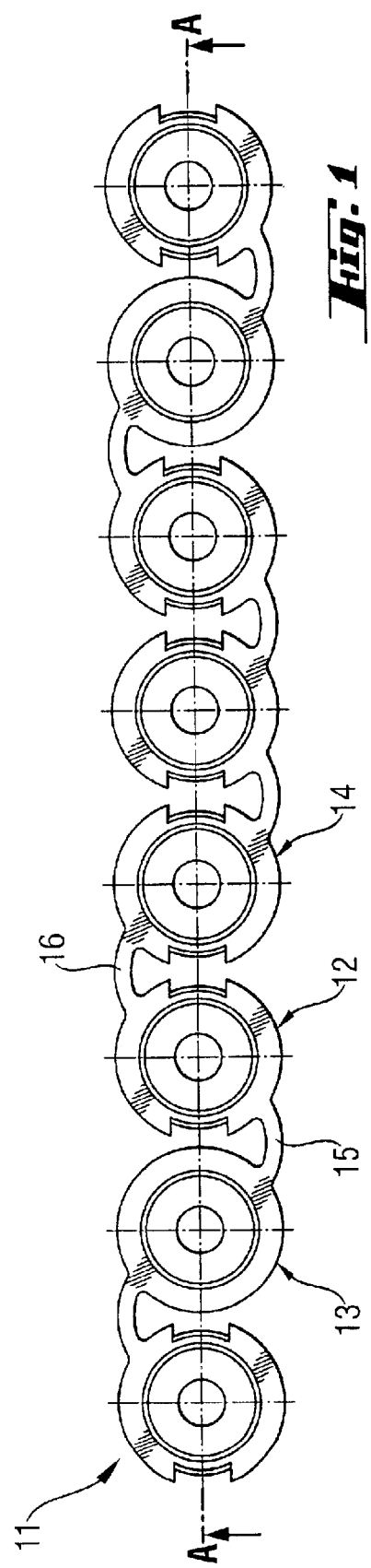
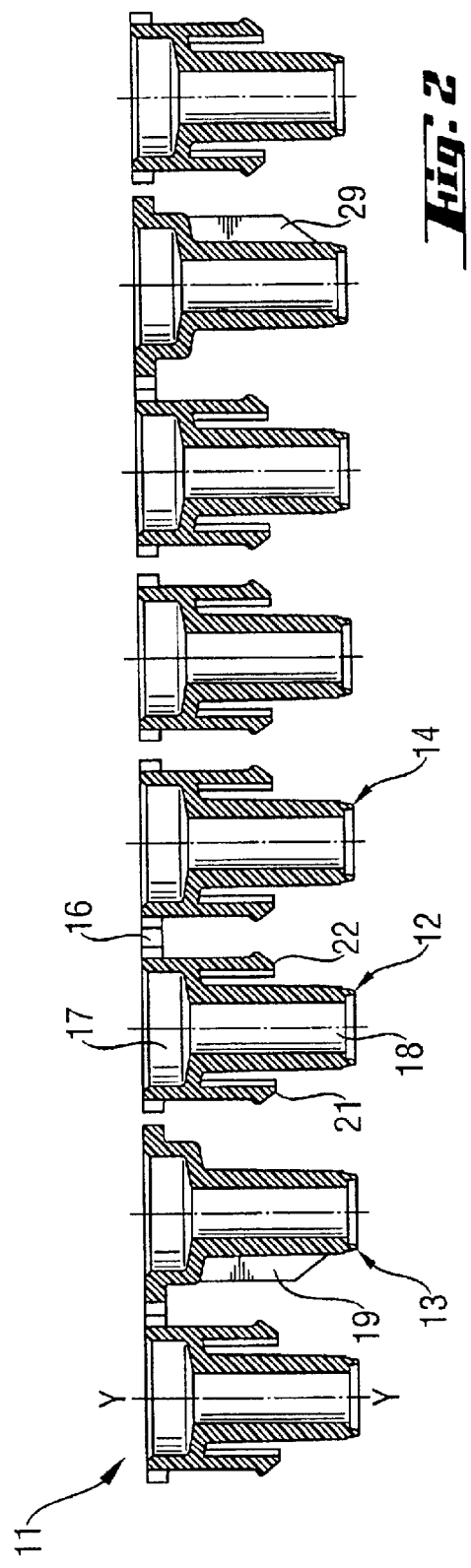

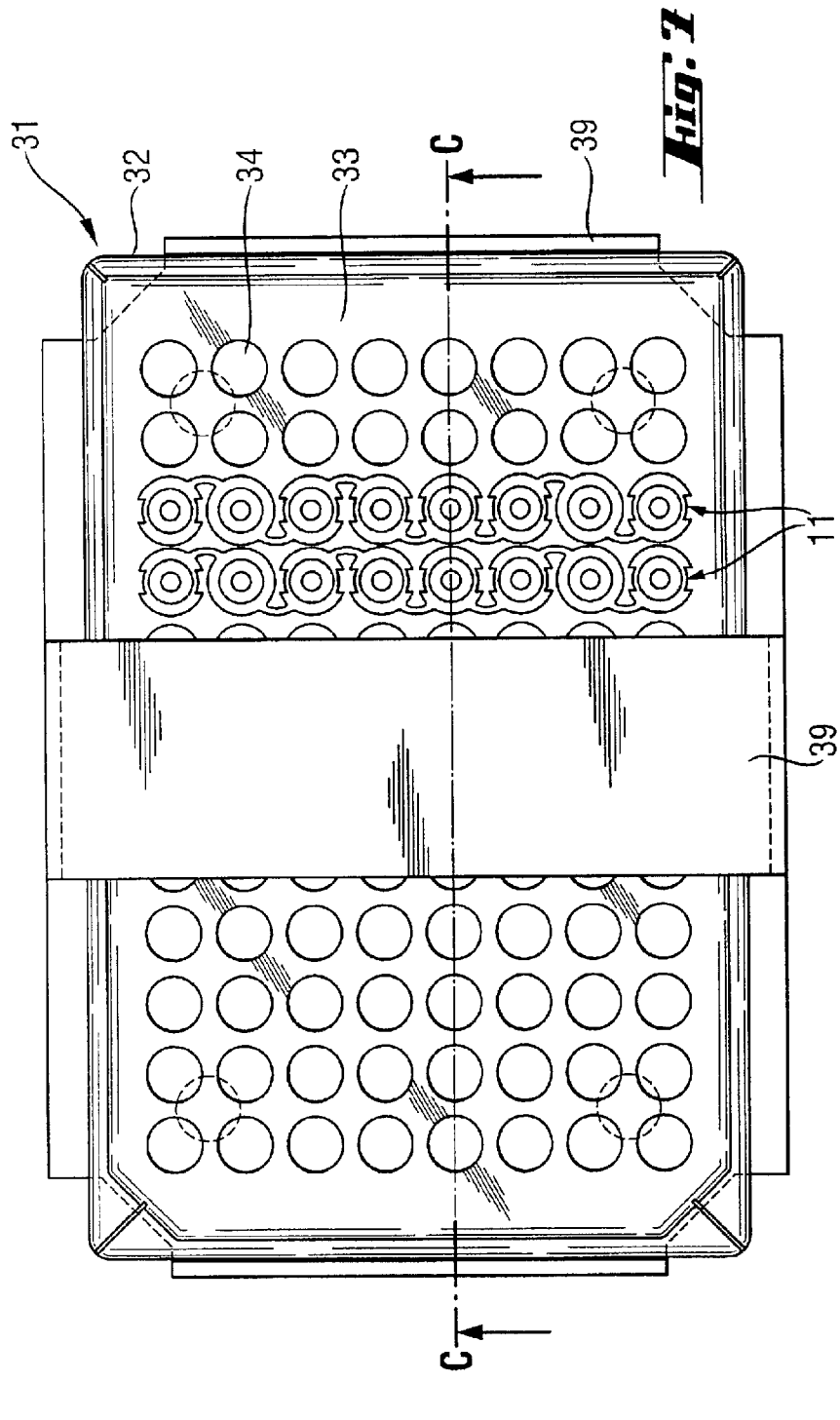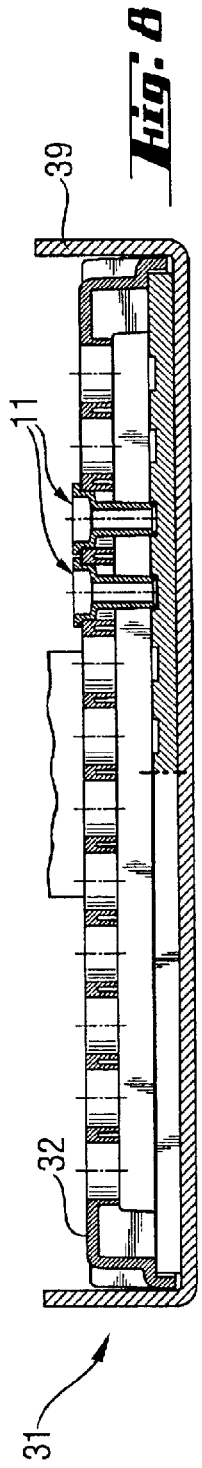

CUVETTE ARRAYS

BACKGROUND OF THE INVENTION

1. Field

The invention relates to linear arrays of cuvettes that are useful for the chemical analysis of samples and the use of such arrays in stackable systems.

2. Description

In the field of chemical analysis of samples, differential expression analysis (profiling) of genes and gene fragments and in particular in the field of screening of pharmaceutical compounds and in bio-diagnostics of such compounds and samples large numbers of such compounds should be analyzed as fast as possible. There is therefore a need for a system of cuvette arrays making it possible to perform diffusion or filtration process steps as well as analytical measurements simultaneously or sequentially on a plurality of liquid samples in order to perform a high throughput screening of those samples.

SUMMARY OF THE INVENTION

The subject invention provides an integrally built, linear array of cuvettes. This array comprises a plurality of adjacent cuvettes arranged along a straight line in an array, each cuvette in the array having the same shape and dimensions, and a plurality of webs. Each cuvette has means that form an integral part thereof and serve to accurately position the cuvette into an opening of a cuvette holder. Each cuvette has means for removably connecting the cuvette to a cuvette holder. In addition, each cuvette has an upper chamber and a lower chamber having a common axis of symmetry passing through the centers of both chambers. Each of the upper and lower chambers have a substantially cylindrical shape, the cross-sectional area of the upper chamber at the central part thereof being larger than the cross-sectional area of the lower chamber. The lower chamber has an open lower end and the upper chamber has an open top end and an annular bottom wall having a central circular opening that connects the upper chamber with the lower chamber. The inner surface of the bottom wall is part of a conical surface and forms an angle of about 80 degrees with the axis of symmetry, so that there is an abrupt change of cross-section between the upper chamber and the lower chamber. The number of webs is one less than the number of cuvettes in the array. Each web connects one adjacent cuvette to another adjacent cuvette so that each cuvette in the array is connected to either one or two other cuvettes. Each web has a curved shape and only a single web joins two adjacent cuvettes. The array of cuvettes is made of a first plastic material which is particularly suitable for being used in combination with a second material out of which a foil-shaped layer is made. The foil-shaped layer being adapted to be closely attached to each cuvette of the array of cuvettes for covering at least one opening of each cuvette.

It is preferred that the symmetry axis of every cuvette forming part of the array of cuvettes lies substantially in a single plane which is a symmetry plane of the cuvette array. The array has two terminal cuvettes and a plurality of intermediate cuvettes. The upper part of each intermediate cuvette of the array is connected by a first single web to a neighboring cuvette lying on one side of the intermediate cuvette and is connected by a second single web to a neighboring cuvette lying on the opposite side of the intermediate cuvette. The first and second single webs lying on opposite sides of the symmetry plane.

The subject invention also provides a two-dimensional array of cuvettes. This array has at least one integrally built, linear array of cuvettes as described above and a cuvette holder having a matrix array of openings configured and dimensioned for receiving the cuvettes, such that each cuvette of the at least one cuvette array fits snugly into one of the openings of the cuvette holder.

It is preferred that this two-dimensional array of cuvettes is where the cuvette holder and the cuvettes of the at least one linear cuvette array are so configured and dimensioned that two or more cuvette holders carrying each at least one linear cuvette array can be stacked in such a way that cuvettes having the same relative position in their respective holders are accurately positioned one above the other with coincidence of their symmetry axis. In this situation, one of the cuvettes takes the position of an upper cuvette and the other cuvette takes the position of a lower cuvette. A portion of the lower part of the upper cuvette lies within the upper chamber of the lower cuvette and the lower end of the upper cuvette is at a predetermined distance from the bottom wall of the upper chamber of the lower cuvette.

It is further beneficial that the two-dimensional array of cuvettes further comprising a foil which is attached to the lower end of each cuvette for covering the opening of the cuvette at that lower end thereof. This foil is beneficially a filter, or is transparent, or carries genes or gene fragments deposited on the foil by microspotting.

Other inventive two-dimensional array of cuvettes are of substantially rectangular shape and have four centering ribs located each on the outer surface of one of the corners of the cuvette holder. Such holder can be configured and dimensioned that the two-dimensional array of cuvettes is adapted to be used in a centrifuge.

BRIEF DESCRIPTION OF THE FIGURES

FIG. 1 Top view of a linear cuvette array 11 according to the invention.

FIG. 2 Cross-section through a plane A—A of linear cuvette array 11 in FIG. 1.

FIG. 7 Top view of a two-dimensional cuvette array 31 according to the invention.

FIG. 8 Cross-section through a plane C—C of two-dimensional cuvette array 31 in FIG. 7.

DETAILED DESCRIPTION OF THE PREFERRED EMBODIMENTS

Figure 3:
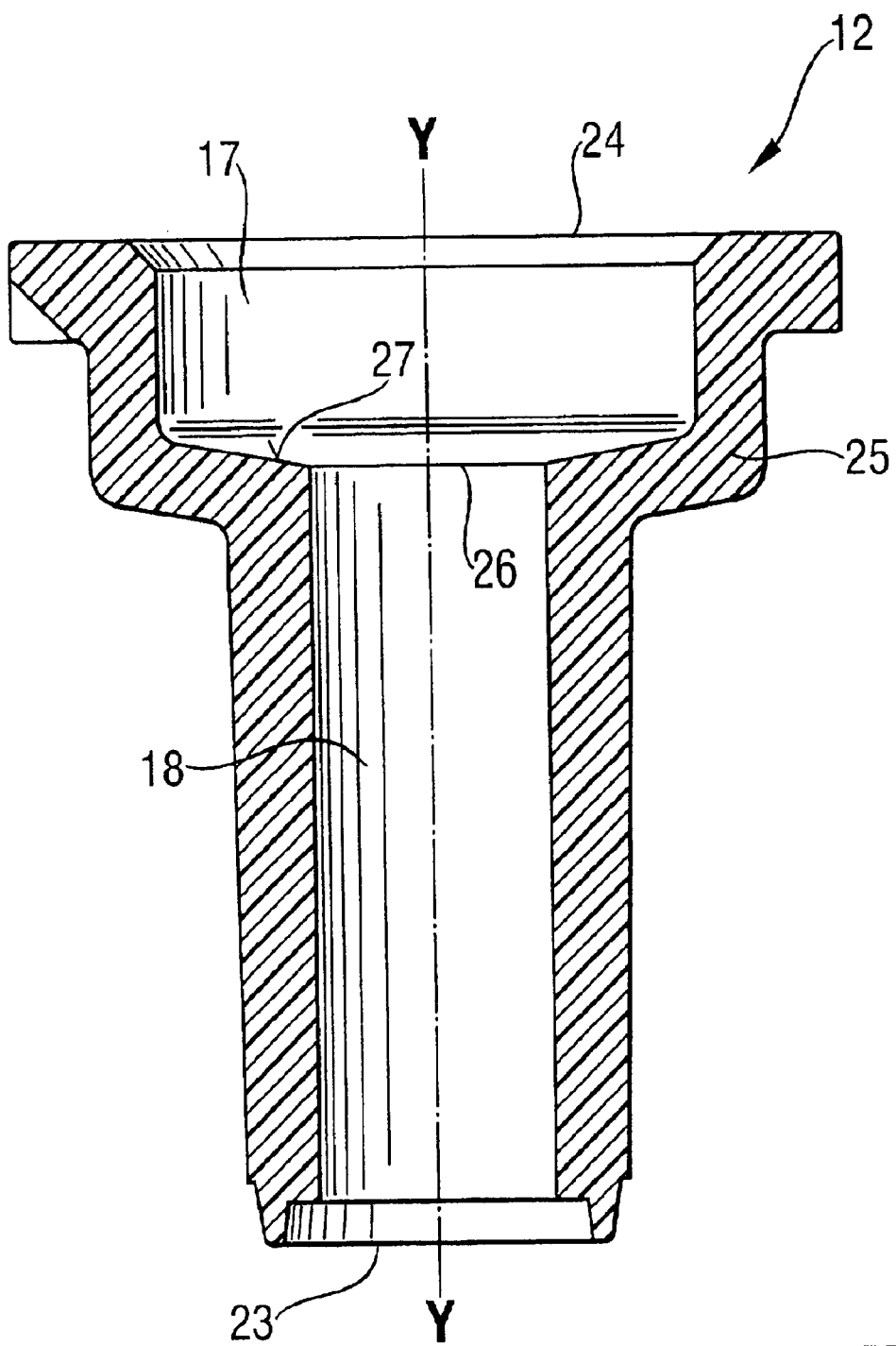
FIG. 3 Cross-sectional view of one of the cuvettes 12 of linear cuvette array 11 in FIG. 1.

The invention will now be described in terms of its preferred embodiments. These embodiments are set forth to aid in understanding the invention but are not to be construed as limiting.

The invention concerns an integrally built, linear array of cuvettes made of a plastic material, every cuvette of the array having the same shape and dimensions, and neighboring cuvettes being connected to each other by a single web.

The invention also concerns a two-dimensional array of cuvettes.

The invention also concerns a system comprising two or more two-dimensional arrays of cuvettes.

The invention may be applicable to several aims—(i) to provide a linear array of cuvettes which is apt to be used as a basic component of such a system, (ii) to provide a two-dimensional array of cuvettes which is apt to be used as a component of such a system, and (iii) to provide a system of cuvette arrays which allows performance of diffusion or filtration process steps as well as analytical measurements simultaneously or sequentially on a plurality of samples and in an optimum way in order to achieve the desired high throughput screening of those samples in an optimum way.

The main advantages of the invention are that it allows the desired process steps to be performed efficiently and with great flexibility, at a relatively low cost, and at the same time makes it possible to overcome problems encountered with prior art devices.

Preferred embodiments of the invention are described hereinafter with reference to the accompanying drawings wherein FIGS. 1 and 2 show an integrally built, linear array 11 of cuvettes 12, 13, 14, etc. made of a plastic material.

Every cuvette of array 11 has the same shape and dimensions and neighboring cuvettes are connected to each other by a single web 15, 16. Each of these single webs 15, 16 has a curved shape.

The symmetry axis Y—Y of every cuvette 12 which forms part of array 11 of cuvettes lies substantially in one and the same plane A—A which is a symmetry plane of cuvette array 11. The upper part of an intermediate cuvette 12 of array 11 is connected by a first single web 15 to a neighboring cuvette 13 which lies on one side of intermediate cuvette 12 and is connected by a second single web 16 to a neighboring cuvette 14 which lies on the opposite side of intermediate cuvette 12. First single web 15 and second single web 16 lie on opposite sides of said symmetry plane A—A.

Webs 15, 16 are flexible and therefore facilitate the insertion of the cuvettes in a cuvette holder, e.g. cuvette holder 32 described hereinafter, in spite of variations of the length of cuvette array 11 which are due to different shrinkage coefficients of the different materials used for manufacture of cuvette arrays 11 by injection molding.

Each one of cuvettes 2 and 7 (this numbers indicate the relative position of the cuvettes of the array) of cuvette array 11 has three radially oriented ribs 19, 29 which serve for accurately positioning the cuvette into an opening of cuvette holder 32 described hereinafter.

Each one of cuvettes 1, 3, 6, 8 or 1, 3–6, 8 (this numbers indicate the relative position of the cuvettes of the array) of cuvette array 11 has e.g. latches 21 and 22 which are an integral part of the cuvette and which serve for removably connecting the cuvette to cuvette holder 32 described hereinafter.

FIG. 2 shows a cross-section of one of the cuvettes, e.g. cuvette 12, of cuvette array 11. As shown by FIG. 2, the cuvette has an upper chamber 17 and a lower chamber 18 which have a common symmetry axis Y—Y which passes through the centers of both chambers. Upper chamber 17 and lower chamber 18 have each a substantially cylindrical shape. The cross-section of upper chamber 17 at the central part thereof is larger than the cross-section of lower chamber 18.

Lower chamber 18 has an open lower end 23. Upper chamber 17 has an open top end 24 and an annular bottom wall 25. This bottom wall has a central circular opening 26 which connects said upper chamber 17 with lower chamber 18.

The inner surface 27 of bottom wall 25 is part of a conical surface the cross-section of which forms an angle of about 80 degrees with the symmetry axis Y—Y of the cuvette, so that there is an abrupt change of cross-section between said upper chamber 17 and said lower chamber 18.

The cuvette array 11 is made by injection molding of a selected first plastic material which is particularly suitable for being used in combination with a second selected material of which a foil shaped layer is made. This layer is adapted to be closely attached to each cuvette of the array of cuvettes for covering at least one opening of each cuvette.

The attachment of the foil shaped layer to each cuvette can be effected e.g. by gluing the layer and the cuvette or by a welding process. The foil attached to each individual cuvette is attached only to this individual cuvette and has no connection with any other cuvette or with a foil attached to a different cuvette.

The attachment of the layer to the cuvette must ensure a medium tight connection (liquid and/or gas tight connection) of these components.

Possible uses of such a foil shaped layer include e.g. its use as a filter and/or as a transparent closure (e.g. transparent to ultraviolet irradiation), which must not necessarily have the function of a filter.

When the foil shaped layer is used as a filter, the filtration process can be effected by use of vacuum or pressure applied to the medium contained in each cuvette of a cuvette array.

Suitable materials for a foil shaped layer usable as a filter and having a thickness in a range of 10 to 200 micrometer are for instance: polyvinylidenfluoride (PVDF), polycarbonate (PC), polysulfone (PSU), regenerated cellulose, polytetrafluorethylene (PTFE), PET, and filter paper.

Figure 4:
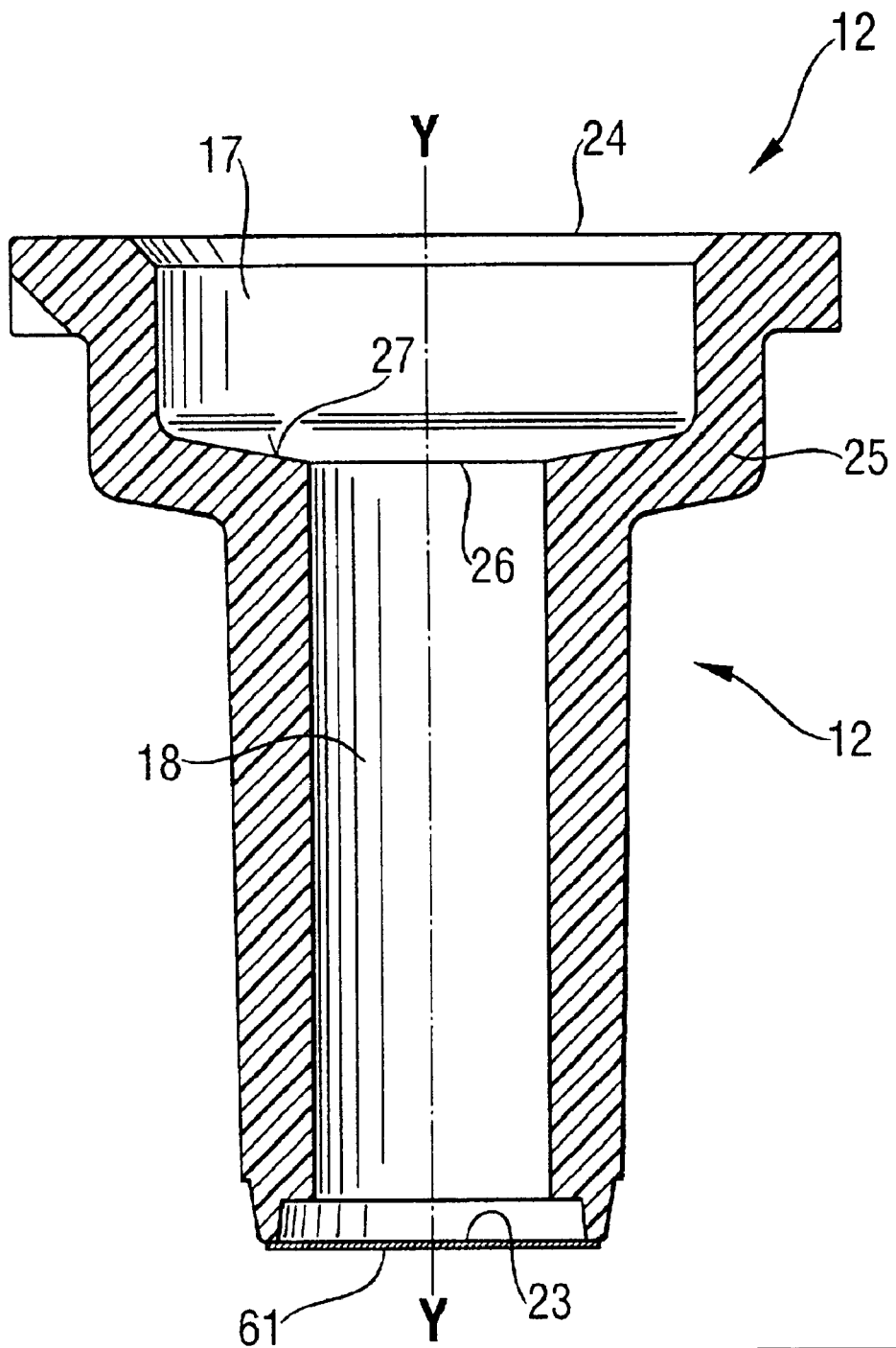
FIG. 4 Cross-sectional view of one of the cuvettes 12 of linear cuvette array 11 in FIG. 1, this cuvette including a foil shaped layer 61 attached to the lower end of the cuvette, FIG. 5 Top view of a cuvette holder 32 forming part of a two-dimensional cuvette array according to the invention.

As shown by FIG. 4 such a foil shaped layer is adapted to be closely attached to the lower end of the cuvette. FIG. 4 shows a cuvette 12 and a foil shaped layer 61 which is closely attached to cuvette 12 for covering the opening of this cuvette at the lower end 23 thereof.

The injection molding apparatus for manufacturing the cuvette array is preferably so configured and dimensioned that injection molding of different materials having different shrinkage coefficients can be carried out with one and the same apparatus.

In order to obtain a high stability of the assembly formed by a cuvette array 11 and the above mentioned foil shaped layer, the material of which this layer is made is so selected that properties of the layer are suitable for use with the material of which the cuvettes are made.

On the other hand the materials of the cuvette array and of the foil shaped layer are so selected that they are particularly well adapted for and thereby enable optimization of a particular process carried out with the assembly of cuvette array and foil shaped layer. Such processes are e.g. filtration, diffusion, concentration determination, "microspotting".

For instance, cuvettes made of an hydrophilic material, e.g. celluloseacetate, are suitably combined with ultrafiltration membranes for carrying out ultrafiltrations in an optimal way. Diffusion processes through artificial membranes are preferably carried out with hydrophobic filtration membranes, which are suitable for being combined by a melting process with cuvette material having similar hydrophobic properties. Filtration processes require hydrophilic or lipophilic properties of the cuvettes and of the filtration membrane attached thereto, and the selection of the materials of these components depends from the properties of the substance to be filtered.

For processes involving genes or genes fragments are deposited by microspotting on the foil which is attached to the lower end of the cuvettes of cuvette array 11.

Following materials are examples of materials which can be used to manufacture cuvette array 11: celluloseacetate, polycarbonate, polyvinylidene fluoride (PVDF), polysulfones, polystyrene, polypropylene (PP). Materials with similar shrinkage coefficient (in connection with injection molding) and melting properties may also be used for manufacturing cuvette array 11.

Figure 5:
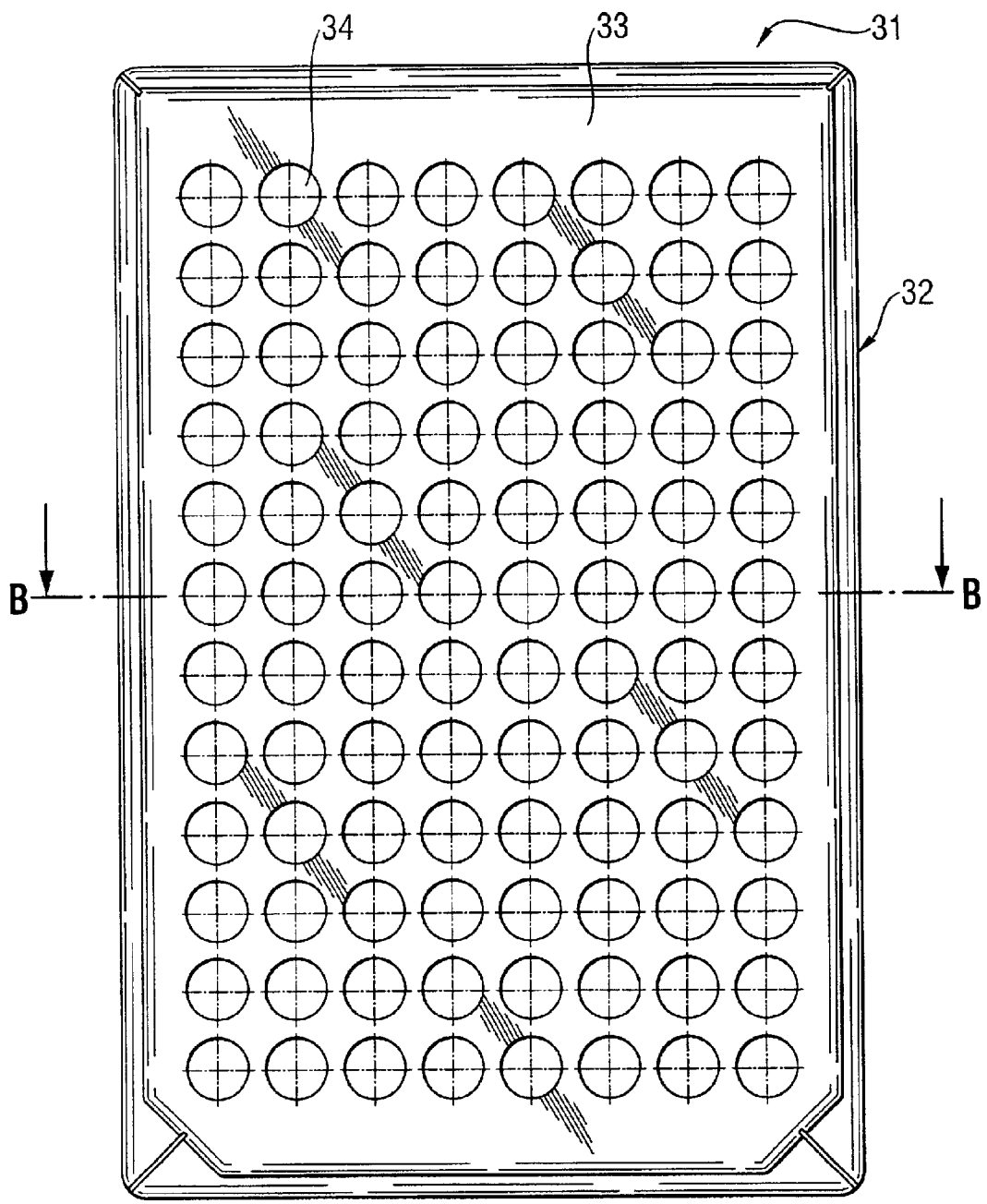
Figure 6:
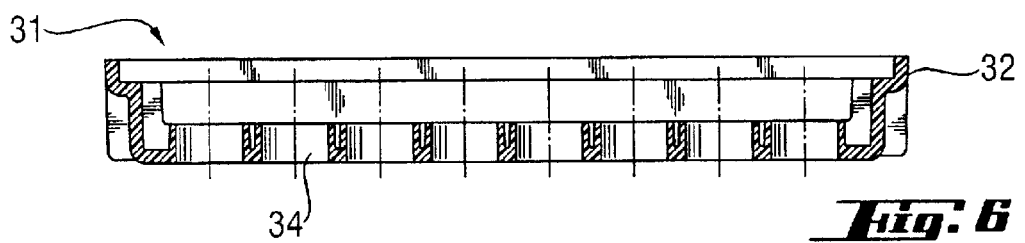
FIG. 6 Cross-section through a plane B—B of cuvette holder 32 in FIG. 5.

FIG. 5 shows a top view of a cuvette holder 32 which can be used to hold a plurality of the above described cuvette arrays 11 to form a two-dimensional cuvette array 31. FIG. 6 shows a cross-section through a plane B—B of cuvette holder 32 in FIG. 5.

In a preferred embodiment, cuvette holder 32 is of substantially rectangular shape and has four centering ribs located each on the outer surface of one of the corners of cuvette holder 32.

FIG. 7 shows a top view of a two-dimensional cuvette array 31 according to the invention. FIG. 8 shows a cross-section through a plane C—C of two-dimensional cuvette array 31 in FIG. 7.

As can be appreciated from FIGS. 7 and 8, a two-dimensional array 31 of cuvettes according to the invention comprises a cuvette holder 32 having a matrix array 33 of openings 34 for receiving cuvettes 12 of at least one linear cuvette array 11 having the above described features. Each of the cuvettes 12 of cuvette array 11 has a shape and dimensions that snugly fits into one of openings 34 of cuvette holder 32.

Cuvette holder 32 is so configured and dimensioned that two-dimensional array 31 is adapted to be used in a centrifugator. As shown by FIG. 8, cuvette holder 32 snugly fits into a holder plate 39 of a centrifuge.

Figure 9:
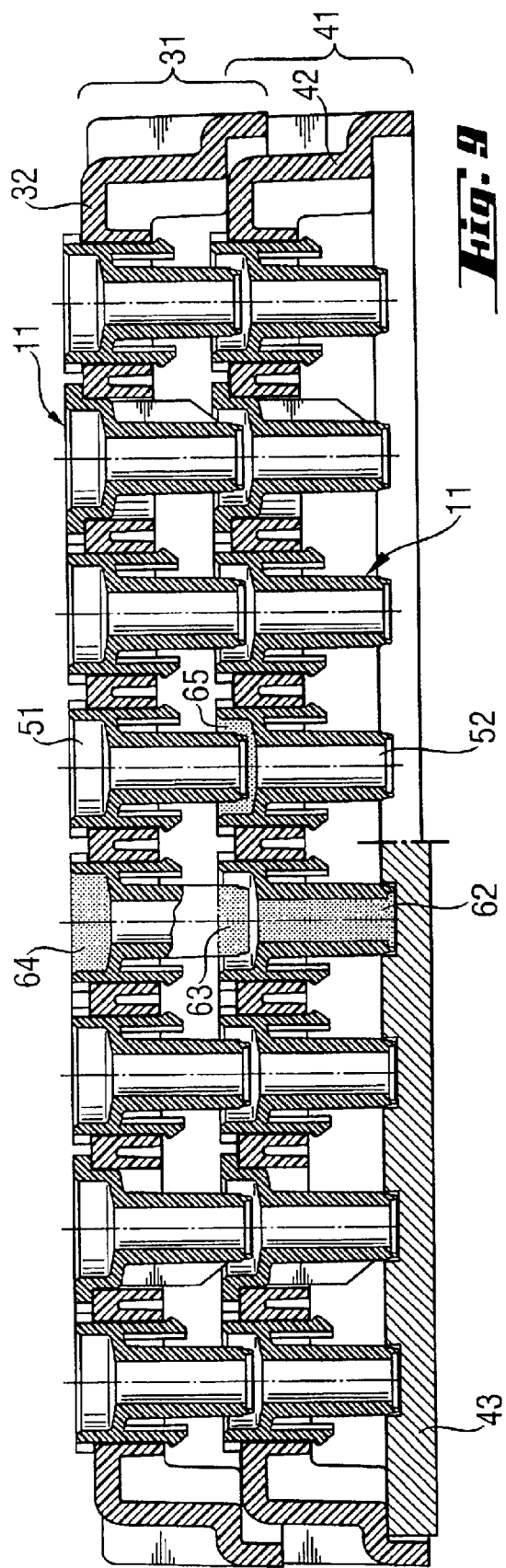
FIG. 9 Cross-sectional representation of stacked two-dimensional cuvette arrays 31 and 41.

As shown by FIG. 9, two or more two-dimensional cuvette arrays e.g. arrays 31 and 41 each of which has the structure described above with reference to FIGS. 7 and 8 and their respective cuvette holders 32, 42 can be stacked on each other to form a three-dimensional cuvette array. Cuvetter holder 42 is positioned on a holder plate 43. According to the invention, the components of such an array are so configured and dimensioned that cuvettes having the same relative position in their respective holders are accurately positioned one above the other with coincidence of their symmetry axis, one of said cuvettes taking the position of an upper cuvette 51 and the other cuvette taking the position of a lower cuvette 52. In a preferred embodiment a portion of the lower part of each upper cuvette 51 lies within the upper chamber of the corresponding lower cuvette 52 and the lower end of the upper cuvette 51 is at a predetermined distance from the bottom wall of the upper chamber of the lower cuvette 52.

In FIG. 9 the following volumes available in the cuvettes are represented by corresponding shaded parts:
a volume 62 available for a sample in a lower cuvette, a volume 63 displaced by the lower part of the upper cuvette in the upper part of the corresponding lower cuvette, a volume 64 available for overflow liquid in the upper part of an upper cuvette, and a volume 65 available for excess liquid in the upper part of a lower cuvette.

Figure 10:
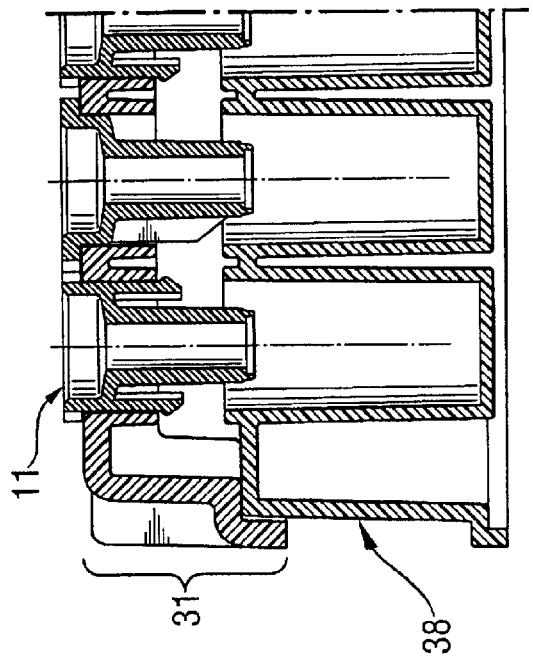
FIG. 10 Cross-sectional representation of a two-dimensional cuvette array 31 stacked onto a standard analysis multiwell plate 38.

As shown by FIG. 10, a two-dimensional cuvette array 31 which has the structure described above with reference to FIGS. 7 and 8 can be stacked also on a standard holder plate 38 for a standard multiwell plate.

According to the invention a system comprising one or more two-dimensional arrays 31, 41, etc. of cuvettes having the above-described structure are used to perform simultaneously diffusion, filtration or detection process steps on a plurality of liquid samples, wherein said samples are e.g. genes, gene fragments, drug substance or precursors of drugs.

In a preferred embodiment such a system comprises a first two-dimensional cuvette array 31 and a second two-dimensional cuvette array 41, said cuvette arrays 31, 41 are stacked on each other, and the cuvette holders 32, 42 and the cuvettes 12 of said two-dimensional cuvette arrays 31, 41 are so configured and dimensioned that cuvettes having the same relative position in their respective holders are accurately positioned one above the other with coincidence of their symmetry axis, one of the cuvettes taking the position of an upper cuvette 51 and the other cuvette taking the position of a lower cuvette 52. In a preferred embodiment a portion of the lower part of the upper cuvette 51 lies within the upper chamber of the lower cuvette 52 and the lower end of the upper cuvette 51 is at a predetermined distance from the bottom wall of the upper chamber of the lower cuvette 52. With this arrangement there is no capillary gap between liquid contained in the lower part of the upper cuvette 51 and liquid contained in the upper chamber of the lower cuvette 52.

| List of reference numbers | |
|---|---|
| 11 | linear cuvette array |
| 12 | cuvette |
| 13 | cuvette |
| 14 | cuvette |
| 15 | web |
| 16 | web |
| 17 | upper chamber |
| 18 | lower chamber |
| 19 | rib |
| 21 | latch |
| 22 | latch |
| 23 | open low end |
| 24 | open top end |
| 25 | bottom wall |
| 26 | opening |
| 27 | inner surface of bottom wall 25 |
| 28 | [not used in text or figures] |
| 29 | rib |
| 31 | two-dimensional cuvette array |
| 32 | cuvette holder |
| 33 | matrix array of openings |
| 34 | opening (for receiving cuvettes) |
| 35 | [not used in text or figures] |
| 36 | [not used in text or figures] |
| 37 | [not used in text or figures] |
| 38 | standard holder plate for a standard multiwell plate |
| 39 | holder plate of a centrifugator |
| 41 | two-dimensional cuvette array |
| 42 | cuvette holder |
| 43 | holder plate |
| 51 | upper cuvette |
| 52 | lower cuvette |
| 61 | foil shaped layer |
| 62 | volume available for a sample |

| | List of reference numbers |
|---|---|
| 63 | displaced volume |
| 64 | volume available for overflow liquid |
| 65 | volume available for excess liquid |

Modifications and alternative embodiments of the invention will be apparent to those skilled in the art in view of the foregoing description. Accordingly, this description is to be construed as illustrative only and is for the purpose of teaching those skilled in the art the best mode of carrying out the invention. Details of the apparatus and of the system described may be varied without departing from the scope and spirit of the invention and the exclusive use of all modifications which come within the scope of the appended claims is reserved.

What is claimed is:

1. An integrally built, linear array of cuvettes, which comprises:
   (a) a plurality of adjacent cuvettes arranged along a straight line in an array, each cuvette in the array having the same shape and dimensions,
      (i) each cuvette has means that form an integral part thereof and serve to accurately position the cuvette into an opening of a cuvette holder,
      (ii) each cuvette has means for removably connecting the cuvette to a cuvette holder,
      (iii) each cuvette has an upper chamber and a lower chamber having a common axis of symmetry passing through the centers of both chambers, each of the upper and lower chambers have a substantially cylindrical shape, the cross-sectional area of the upper chamber at the central part thereof being larger than the cross-sectional area of the lower chamber, the lower chamber has an open lower end, the upper chamber has an open top end and an annular bottom wall having a central circular opening that connects the upper chamber with the lower chamber, the inner surface of the bottom wall is part of a conical surface which forms an angle of about 80 degrees with the axis of symmetry, so that there is an abrupt change of cross-section between the upper chamber and the lower chamber;
   (b) a plurality of webs, the number of webs being one less than the number of cuvettes in the array, each web connecting one adjacent cuvette to another adjacent cuvette so that each cuvette in the array is connected to either one or two other cuvettes, each web has a curved shape and only a single web joins two adjacent cuvettes; and
   (c) the array of cuvettes is made of a first plastic material which is particularly suitable for being used in combination with a second material out of which a foil-shaped layer is made, the foil-shaped layer being adapted to be closely attached to each cuvette of the array of cuvettes for covering at least one opening of each cuvette.

2. The cuvette array according to claim 1, wherein the symmetry axis of every cuvette forming part of the array of cuvettes lies substantially in a single plane which is a symmetry plane of the cuvette array, the array having two terminal cuvettes and a plurality of intermediate cuvettes, the upper part of each intermediate cuvette of the array is connected by a first single web to a neighboring cuvette lying on one side of the intermediate cuvette and is connected by a second single web to a neighboring cuvette lying on the opposite side of the intermediate cuvette, the first and second single webs lying on opposite sides of the symmetry plane.

3. A two-dimensional array of cuvettes, which comprises:
   I. at least one integrally built, linear array of cuvettes, comprising:
      (d) a plurality of adjacent cuvettes arranged along a straight line in an array, each cuvette in the array having the same shape and dimensions,
         (iv) each cuvette has means that form an integral part thereof and serve to accurately position the cuvette into an opening of a cuvette holder,
         (v) each cuvette has means for removably connecting the cuvette to a cuvette holder,
         (vi) each cuvette has an upper chamber and a lower chamber having a common axis of symmetry passing through the centers of both chambers, each of the upper and lower chambers have a substantially cylindrical shape, the cross-sectional area of the upper chamber at the central part thereof being larger than the cross-sectional area of the lower chamber, the lower chamber has an open lower end, the upper chamber has an open top end and an annular bottom wall having a central circular opening that connects the upper chamber with the lower chamber, the inner surface of the bottom wall is part of a conical surface, the cross-section of which forms an angle of about 80 degrees with the axis of symmetry, so that there is an abrupt change of cross-section between the upper chamber and the lower chamber;
      (e) a plurality of webs, the number of webs being one less than the number of cuvettes in the array, each web connecting one adjacent cuvette to another adjacent cuvette so that each cuvette in the array is connected to either one or two other cuvettes, each web has a curved shape and only a single web joins two adjacent cuvettes; and
      (f) the array of cuvettes is made of a first plastic material which is particularly suitable for being used in combination with a second material out of which a foil-shaped layer is made, the foil-shaped layer being adapted to be closely attached to each cuvette of the array of cuvettes for covering at least one opening of each cuvette;
   II. a cuvette holder having a matrix array of openings configured and dimensioned for receiving the cuvettes, such that each cuvette of the at least one cuvette array fits snugly into one of the openings of the cuvette holder.

4. The two-dimensional array of cuvettes according to claim 3, wherein the cuvette holder and the cuvettes of the at least one linear cuvette array are so configured and dimensioned that two or more cuvette holders carrying each at least one linear cuvette array can be stacked in such a way that cuvettes having the same relative position in their respective holders are accurately positioned one above the other with coincidence of their symmetry axis, one of the cuvettes taking the position of an upper cuvette and the other cuvette taking the position of a lower cuvette, a portion of the lower part of the upper cuvette lying within the upper chamber of the lower cuvette and the lower end of the upper cuvette being at a predetermined distance from the bottom wall of the upper chamber of the lower cuvette.

5. The two-dimensional array of cuvettes according to claim 4, further comprising a foil which is attached to the lower end of each cuvette for covering the opening of the cuvette at that lower end thereof.

6. The two-dimensional array of cuvettes according to claim 5, wherein the foil is a filter.

7. The two-dimensional array of cuvettes according to claims 5, wherein the foil is transparent.

8. The two-dimensional array of cuvettes according to claims 5, wherein the foil carries genes or gene fragments deposited on the foil by microspotting.

9. The two-dimensional array of cuvettes according to claim 4, wherein the cuvette holder is of substantially rectangular shape and has four centering ribs located each on the outer surface of one of the corners of the cuvette holder.

10. The two-dimensional array of cuvettes according to claim 4, wherein the cuvette holder is so configured and dimensioned that the two-dimensional array of cuvettes is adapted to be used in a centrifuge.

* * * * *